United States Patent
Zwaans et al.

(10) Patent No.: US 9,354,332 B2
(45) Date of Patent: May 31, 2016

(54) DETECTOR ARRAY WITH TIME-TO-DIGITAL CONVERSION HAVING IMPROVED TEMPORAL ACCURACY

(75) Inventors: Bernardus Antonius Maria Zwaans, Rosmalen (NL); Thomas Frach, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 67 days.

(21) Appl. No.: 14/009,666

(22) PCT Filed: Mar. 29, 2012

(86) PCT No.: PCT/IB2012/051506
§ 371 (c)(1),
(2), (4) Date: Oct. 3, 2013

(87) PCT Pub. No.: WO2012/137109
PCT Pub. Date: Oct. 11, 2012

(65) Prior Publication Data
US 2014/0021356 A1  Jan. 23, 2014

Related U.S. Application Data

(60) Provisional application No. 61/471,914, filed on Apr. 5, 2011.

(51) Int. Cl.
*G01T 1/29* (2006.01)
*G04F 10/00* (2006.01)
*A61B 6/03* (2006.01)

(52) U.S. Cl.
CPC ............ *G01T 1/2985* (2013.01); *G04F 10/005* (2013.01); *A61B 6/037* (2013.01)

(58) Field of Classification Search
CPC ....... G01T 1/2985; G01T 1/248; G01T 1/247; G01T 1/648; G01T 7/005; H01J 49/40; H01J 49/0036; G04F 10/005; G04F 10/00
USPC .............. 250/363.03, 287, 363.04, 282, 362, 250/363.09; 341/166, 156; 702/189, 187
See application file for complete search history.

(56) References Cited

U.S. PATENT DOCUMENTS 3,081,447 A * 3/1963 Sierra ..................... G06F 3/08
                                                    360/39
6,760,764 B1 * 7/2004 Driediger ................. G06F 1/14
                                                    709/204
(Continued)

FOREIGN PATENT DOCUMENTS

WO    2009019660 A2    2/2009
WO    2009083501 A2    7/2009
(Continued)

OTHER PUBLICATIONS

Maymandi-Nejad et al.; A Digitally Programmable Delay Element: Design and Analysis; 2003; IEEE Trans. on Very Large Scale Integration Systems; 11(5)871-878.

(Continued)

*Primary Examiner* — David Porta
*Assistant Examiner* — Blake Riddick

(57) ABSTRACT

A detector (22) detects an event. First and second time-to-digital converters (TDCs) (70, 72) generate first and second time stamps (TS1, TS2) for the detection of the event. The first TDC and the second TDC are both synchronized with a common clock signal (62) that defines a fixed time offset between the second TDC and the first TDC. An autocalibration circuit (120) adjusts the first TDC and the second TDC to keep the time difference between the second time stamp and the first time stamp equal to the fixed time offset between the second TDC and the first TDC. The detector may be a detector array, and trigger circuitry (28) propogates a trigger signal from a trigger detector of the array of detectors to the first and second TDC's. Skew correction circuitry (132, 134, 136, 142, 60, 162) adjusts a timestamp (TS) based on which detector is the triggering detector.

18 Claims, 8 Drawing Sheets

(56) References Cited

U.S. PATENT DOCUMENTS

Figure 1:
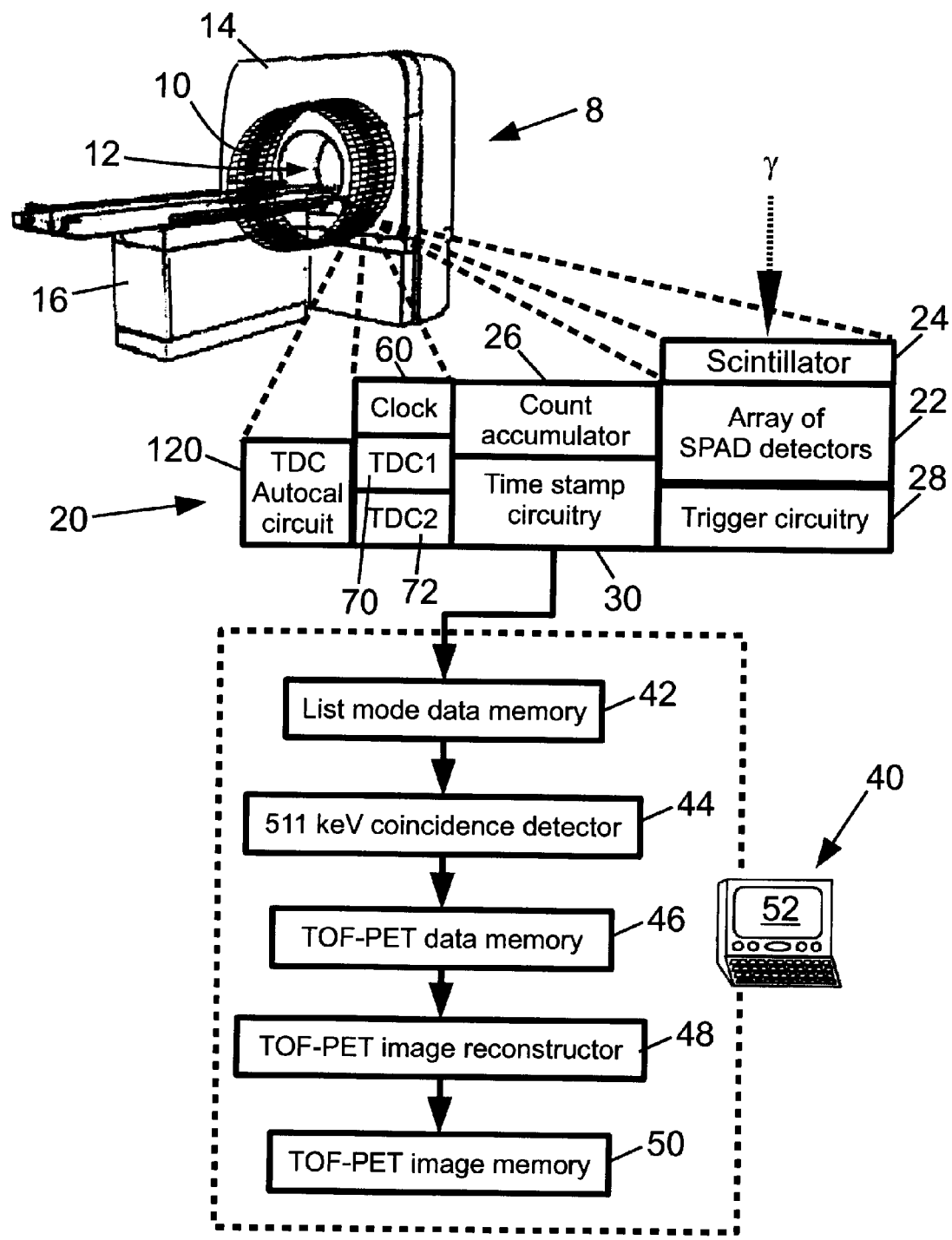

| | | | |
|---|---|---|---|
| 7,129,495 B2 * | 10/2006 | Williams | G01T 1/2985 250/363.03 |
| 7,268,599 B1 * | 9/2007 | Hwang | 327/156 |
| 7,429,944 B1 * | 9/2008 | Nairn | 341/155 |
| 7,626,389 B2 | 12/2009 | Fiedler et al. | |
| 7,723,694 B2 | 5/2010 | Frach et al. | |
| 7,932,847 B1 * | 4/2011 | Hsieh et al. | 341/155 |
| 8,106,808 B1 * | 1/2012 | Cohen et al. | 341/166 |
| 8,395,127 B1 | 3/2013 | Frach et al. | |
| 8,399,848 B2 | 3/2013 | Frach et al. | |
| 2003/0152177 A1 * | 8/2003 | Cahill-O'Brien | H04J 3/0664 375/354 |
| 2004/0133374 A1 * | 7/2004 | Kattan | G01R 31/31717 702/85 |
| 2006/0103566 A1 | 5/2006 | Vemulapalli et al. | |
| 2006/0145082 A1 * | 7/2006 | Stearns | G01T 1/2985 250/363.03 |
| 2007/0270693 A1 * | 11/2007 | Fiedler | G01T 1/208 600/436 |
| 2007/0273569 A1 * | 11/2007 | Lin | 341/155 |
| 2009/0219073 A1 * | 9/2009 | Sun et al. | 327/285 |
| 2009/0236532 A1 | 9/2009 | Frach et al. | |
| 2010/0182011 A1 | 7/2010 | Prescher et al. | |
| 2010/0252723 A1 | 10/2010 | Frach et al. | |
| 2011/0001053 A1 * | 1/2011 | Solf | G01T 1/249 250/370.08 |
| 2011/0210255 A1 * | 9/2011 | Kim | G01T 1/2985 250/362 |
| 2011/0278466 A1 | 11/2011 | Frach et al. | |
| 2012/0056961 A1 * | 3/2012 | Kinoshita | G06K 15/1247 347/118 |
| 2012/0068077 A1 | 3/2012 | Frach et al. | |

FOREIGN PATENT DOCUMENTS

| | | |
|---|---|---|
| WO | 2010032184 A2 | 3/2010 |
| WO | 2010136910 A2 | 12/2010 |
| WO | WO 2010136910 A2 * | 12/2010 |

OTHER PUBLICATIONS

ACAM; Time-to-Digital Converters; Product Overview; Nov. 2010; www.acam.de/fileadmin/Download/.../acam_product_overview_e.pdf, Published by the company acam.

Mota, M., et al.; A four channel, self-calibrating, high resolution, Time to Digital Converter; 1998; http://cdsweb.cern.ch/record/354075/filed/ep-98-049.pdf, Published by IEEE.

Wu, J., et al.; The 10-ps Wave Union TDC: Improving FPGA TDC Resolution beyond Its Cell Delay; downloaded Mar. 16, 2011; www.ppd.fnal.gov/EEDOffice-W/Projects/ckm/.../PID765918.pdf, Published by IEEE in 2008.

* cited by examiner

DETECTOR ARRAY WITH TIME-TO-DIGITAL CONVERSION HAVING IMPROVED TEMPORAL ACCURACY

CROSS REFERENCE TO RELATED APPLICATIONS

This application is a national filing of PCT application Serial No. PCT/IB2012/051506, filed Mar. 29, 2012, published as WO 2012/137109 A2 on Oct. 11, 2012, which claims the benefit of U.S. provisional application Ser. No. 61/471,914 filed Apr. 5, 2011, which is incorporated herein by reference.

The following relates to the radiation detection arts. It particularly relates to high-speed radiation detectors for positron emission tomography (PET), especially time-of-flight (TOF) PET, and will be described with particular reference thereto. However, the following relates more generally to high speed radiation detectors for other types of radiological imaging, as well as to high-speed radiation detectors for other applications such as astronomy.

In PET imaging, a radiopharmaceutical administered to a human patient or other imaging subject emits positrons, each of which in turn annihilates with an electron of the surrounding imaging subject in an electron-positron annihilation event to produce two oppositely directed 511 keV gamma rays. In conventional PET imaging these two oppositely directed gamma rays are detected by radiation detectors surrounding the imaging subject as two substantially simultaneous radiation detection events that define a line of response (LOR) therebetween. In time-of-flight (TOF) PET, the small time difference (or lack thereof) between the two substantially simultaneous detection events is used to further localize the positron along the LOR.

To provide useful TOF localization, the 511 keV gamma rays should be detected with sub-nanosecond temporal resolution. Radiation detectors capable of achieving these speeds include photomultiplier tube (PMT) detectors and silicon-based single-photon avalanche diode (SPAD) detectors (also sometimes referred to as an avalanche photodiode or APD operating in Geiger mode). Such detectors typically perform detection of the 511 keV gamma rays in conjunction with a scintillator. SPAD detectors advantageously leverage mature silicon microelectronics fabrication technology to enable monolithic integration of a two-dimensional detector array on a silicon substrate. Time stamping circuitry may be integrated monolithically on the same silicon substrate as the SPAD array, or may be formed on a separate silicon substrate that is operatively connected with the SPAD array as a hybrid circuit. This is advantageous since the time stamp electronics should be located with the SPAD array, for example on the PET detector gantry, and preferably either on the same chip as the SPAD array or close to it (e.g., as a 3D stack of chips). Some illustrative examples of SPAD detector arrays for TOF-PET or other high-speed applications are disclosed in: Frach et al., U.S. Pat. No. 7,723,694 issued May 25, 2010 which is incorporated herein by reference in its entirety; Fiedler et al, U.S. Pat. No. 7,626,389 issued Dec. 1, 2009 which is incorporated herein by reference in its entirety; and Prescher et al., U.S. Pub. No. 2010/0182011 A1 published Jul. 22, 2010 which is incorporated herein by reference in its entirety.

Although radiation detectors such as PMT or SPAD detectors are capable of sub-nanosecond temporal resolution, actually achieving this is contingent upon providing suitable electronics including time-stamping circuitry. In one approach, triggering circuitry generates a signal pulse or other trigger signal at the time of detection. In the case of a scintillator/detector array configuration, a single 511 keV gamma ray produces a scintillation comprising many photons in the optical or other wavelength range, and a single "pixel" of the detector array comprises a sub-array of SPAD detectors that accumulate a photon count corresponding to the 511 keV gamma ray. In such cases, the trigger circuitry is designed to trigger on the first detected photon or on some other trigger criterion such as the tenth detected photon or so forth.

However the trigger is configured, the time stamp circuitry relates the time of the trigger signal to a system clock to provide the time stamp. However, the time resolution of the system clock may be too coarse for TOF PET. For example, a system clock operating at 200 MHz produces a clock pulse every 5 ns, which is insufficient for sub-nanosecond timestamp resolution. In such cases, the system clock is treated as a coarse counter and a fine counter is provided to assess temporal offset of the trigger signal from a reference point of the clock (e.g., rising edge of the clock pulse, or falling edge of the clock pulse).

The approaches are found to provide sufficient (e.g., sub-nanosecond) temporal resolution for a given radiation detector pixel at a given time. However, spatial variation across the detector array, also called "skew", can produce substantial errors. Also, voltage and/or temperature variation can cause drift in the output of the fine counter over time. The combination of skew and temporal drift can substantially degrade the effective temporal resolution of the PET detector array.

The following contemplates improved apparatuses and methods that overcome the aforementioned limitations and others.

According to one aspect, a method comprises: detecting an event; generating a trigger signal associated with the detection of the event; generating a first time stamp for the trigger signal using a first time to digital converter (TDC); generating a second time stamp for the trigger signal using a second TDC having a fixed time offset respective to the first TDC; and associating a time stamp with the event based on the first time stamp, the second time stamp, and a comparison of (1) the time difference between the second time stamp and the first time stamp and (2) the fixed time offset. In some such methods the first TDC is synchronized with a common clock signal, the second TDC is synchronized with the common clock signal, and the synchronizing operations determine the fixed time offset of the second TDC respective to the first TDC as the period of the common clock signal or as a fixed fraction or multiple of the period of the common clock signal. In some such embodiments the detecting comprises detecting a radiation particle using an array of positron emission tomography (PET) detectors, and the method further comprises: repeating the detecting, generating of the trigger signal, generating of first and second time stamps, and associating to acquire a data set of time stamped radiation detection events; generating a time of flight (TOF) PET data set from the data set of time stamped radiation detection events; and reconstructing the TOF PET data set to generate a PET image.

According to another aspect, an apparatus comprises: a detector configured to detect an event; a first time to digital converter (TDC) configured to generate a first time stamp for the detection of the event; a second TDC configured to generate a second time stamp for the detection of the event, there being a fixed time offset between the second TDC and the first TDC; and an autocalibration circuit configured to adjust the first TDC and the second TDC to keep the time difference between the second time stamp and the first time stamp equal to the fixed time offset between the second TDC and the first TDC. In some such apparatus the first TDC and the second TDC are both synchronized with a common clock signal that defines the fixed time offset between the second TDC and the first TDC. In some such apparatus the first TDC measures a first time interval and transforms the first time interval into the first time stamp using a first transform operation, the second TDC measures a second time interval and transforms the second time interval into the second time stamp using a second transform operation, and the autocalibration circuit adjusts the first and second transform operations to keep the time difference between the second time stamp and the first time stamp equal to the fixed time offset between the second TDC and the first TDC. In some such apparatus the first transform operation includes applying a first look-up table and the second transform operation includes applying a second look-up table.

According to another aspect, a positron emission tomography (PET) system includes radiation detectors comprising the apparatus set forth in the immediately preceding paragraph and a processor configured to generate time of flight (TOF) PET data from the output of the radiation detectors and to reconstruct the TOF PET data to generate an image.

According to another aspect, an apparatus comprises: an array of detectors configured to detect an event; trigger circuitry configured to propagate a trigger signal associated with the detection of the event from a triggering detector of the array of detectors to time stamp circuitry configured to generate a time stamp for the detection of the event; and skew correction circuitry configured to adjust the time stamp based on which detector is the triggering detector. In some such apparatus the skew correction circuitry comprises delay elements incorporated into the trigger circuitry to delay the propagation of the trigger signal to the time stamp circuitry based on which detector is the triggering detector. In some such apparatus the skew correction circuitry is configured to adjust the generated time stamp based on a skew correction look-up table tabulating the skew correction for each detector of the array of detectors.

According to another aspect, in an apparatus as set forth in the immediately preceding paragraph the time stamp circuitry comprises: a first time to digital converter (TDC) configured to generate a first time stamp for the detection of the event based on the trigger signal; a second TDC configured to generate a second time stamp for the detection of the event based on the trigger signal; and an autocalibration circuit configured to adjust the first TDC and the second TDC to keep the time difference between the second time stamp and the first time stamp equal to a predetermined fixed time offset between the second TDC and the first TDC.

One advantage resides in providing improved temporal resolution for radiation detection events.

Another advantage resides in providing more accurate time-of-flight PET imaging.

Another advantage resides in providing automatic self-calibration of time-to-digital converter (TDC) devices.

Another advantage resides in providing improved spatial/temporal resolution for a radiation detector array.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagramatically shows a time-of-flight positron emission tomography (TOF-PET) system.

Figure 2:
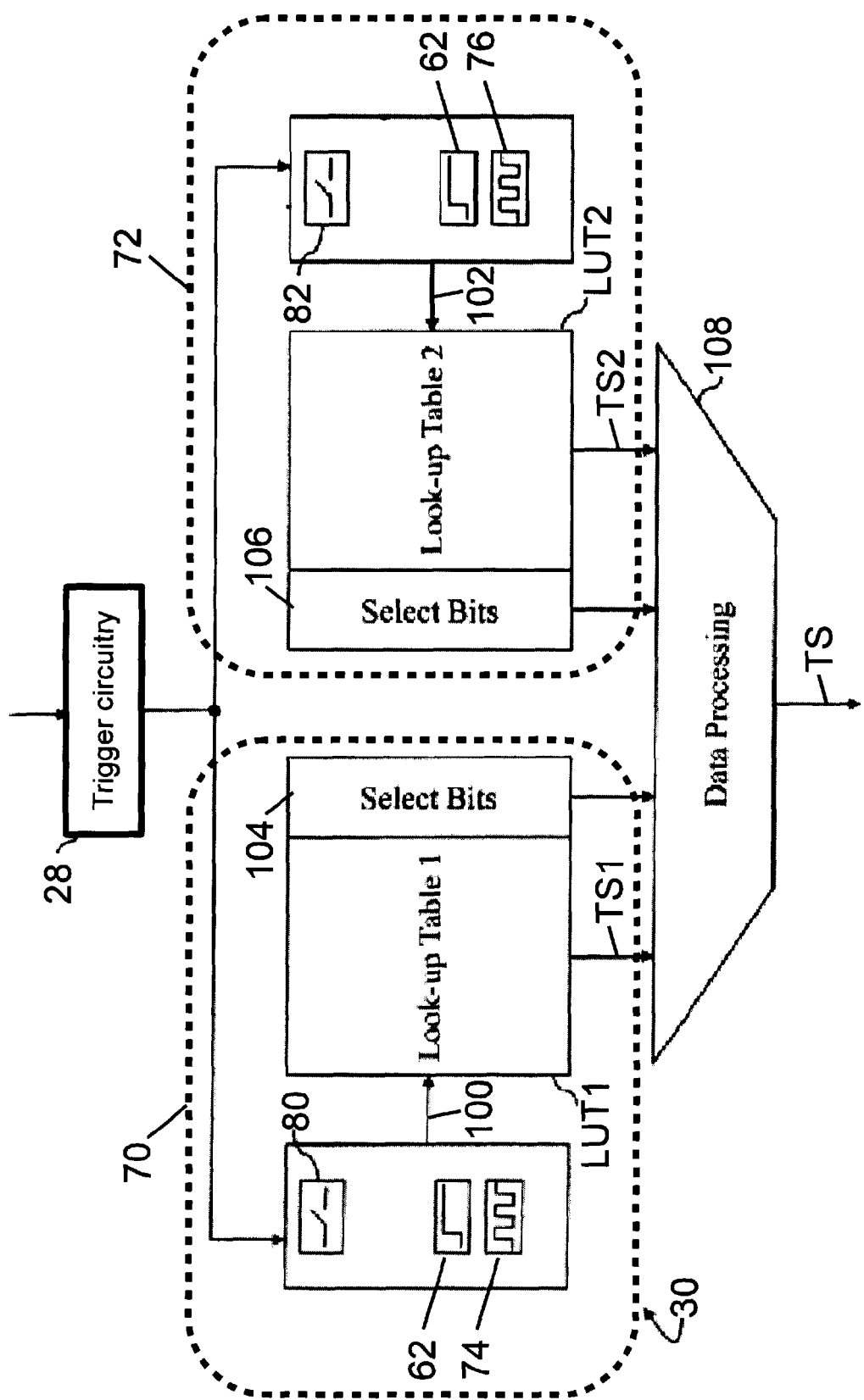

FIG. 2 diagramatically shows time stamp sub-circuitry the radiation detectors of the TOF-PET system of FIG. 1.

Figure 3:
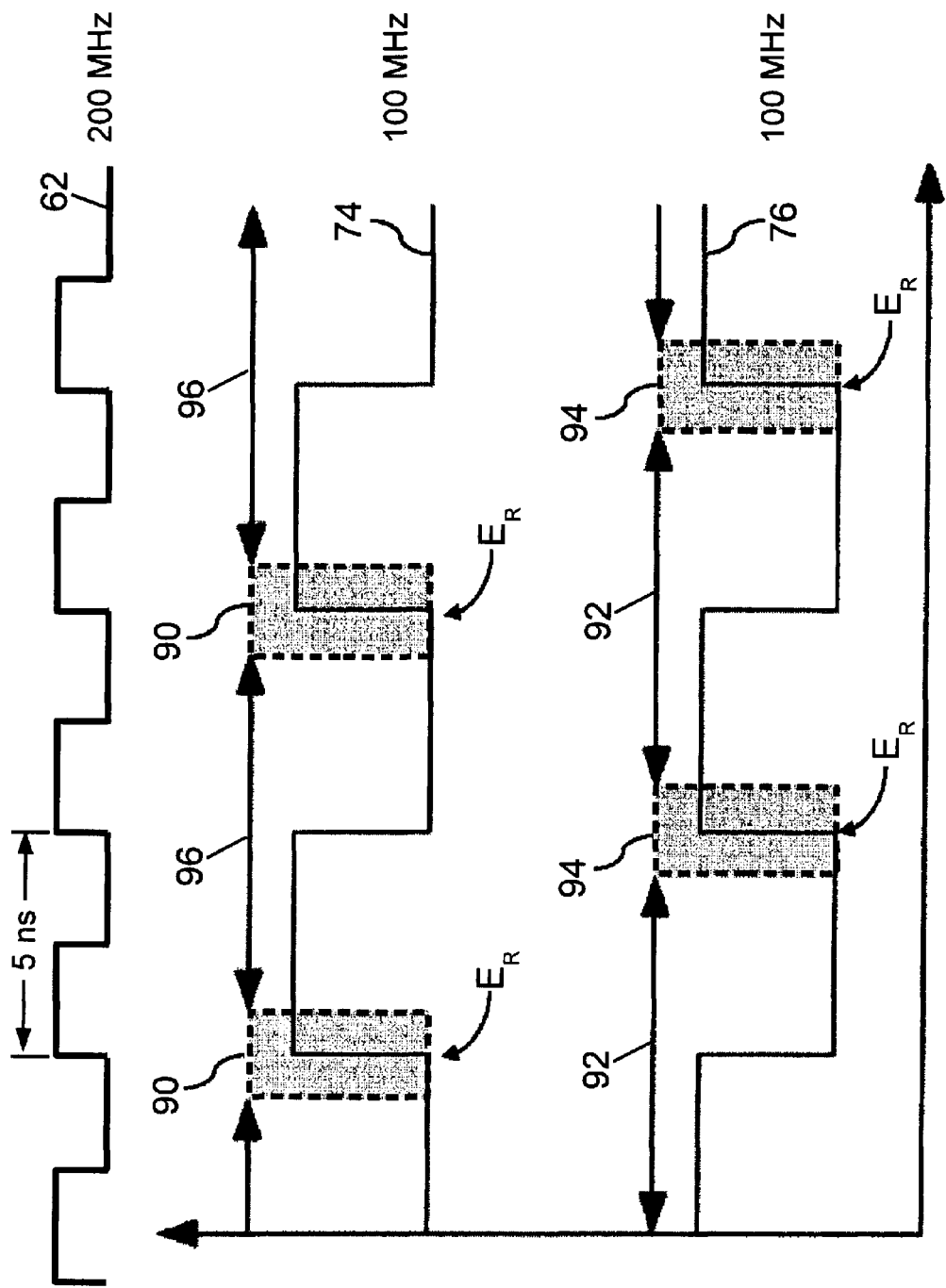

FIG. 3 diagramatically shows timing pulses of the system clock and first and second time-to-digital converter (TDC) devices.

Figure 4:
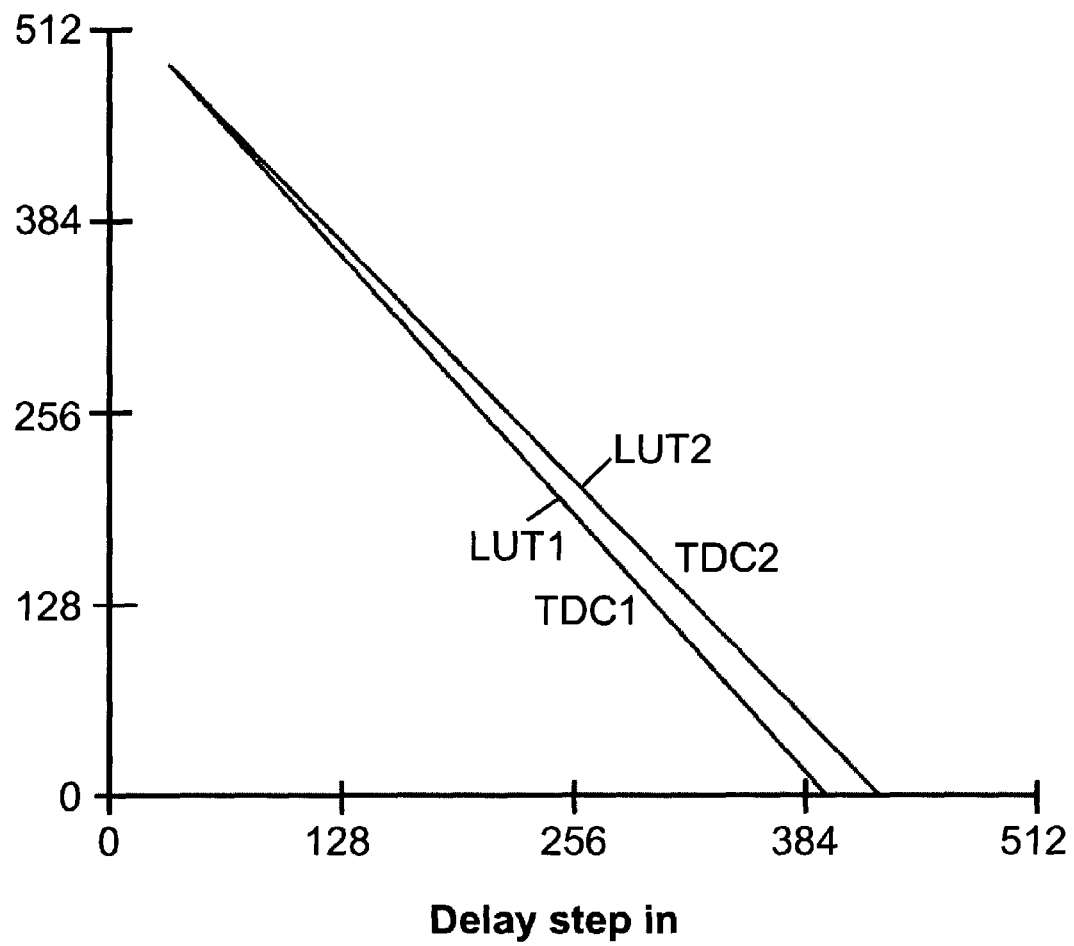

FIG. 4 diagramatically shows typical look-up table (LUT) values for first and second TDC's.

Figure 5:
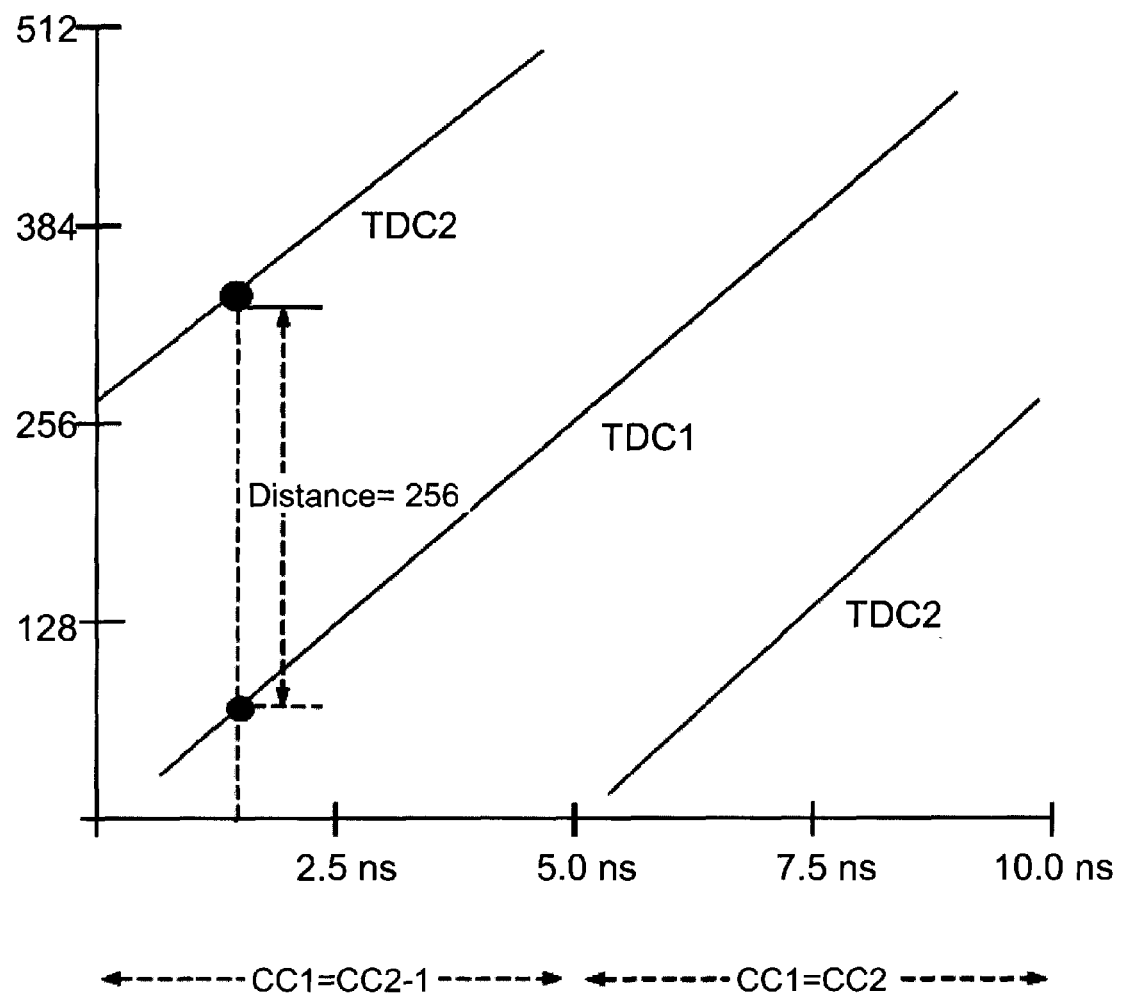

FIG. 5 diagramatically shows time stamp processing using the TDC's of FIG. 1.

Figure 6:
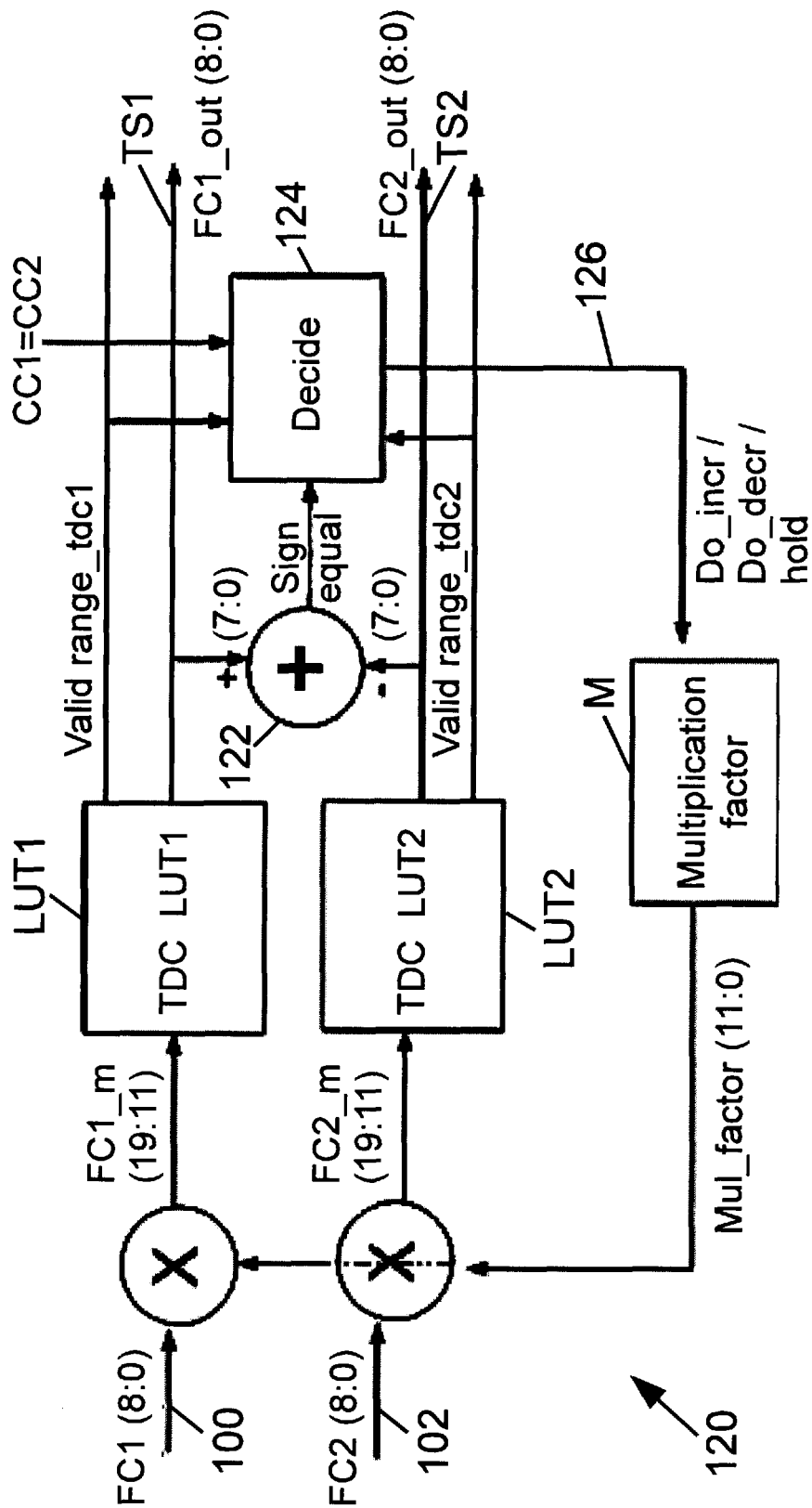

FIG. 6 diagramatically shows an illustrative embodiment of the TDC autocalibration circuit of FIG. 1.

Figure 7:
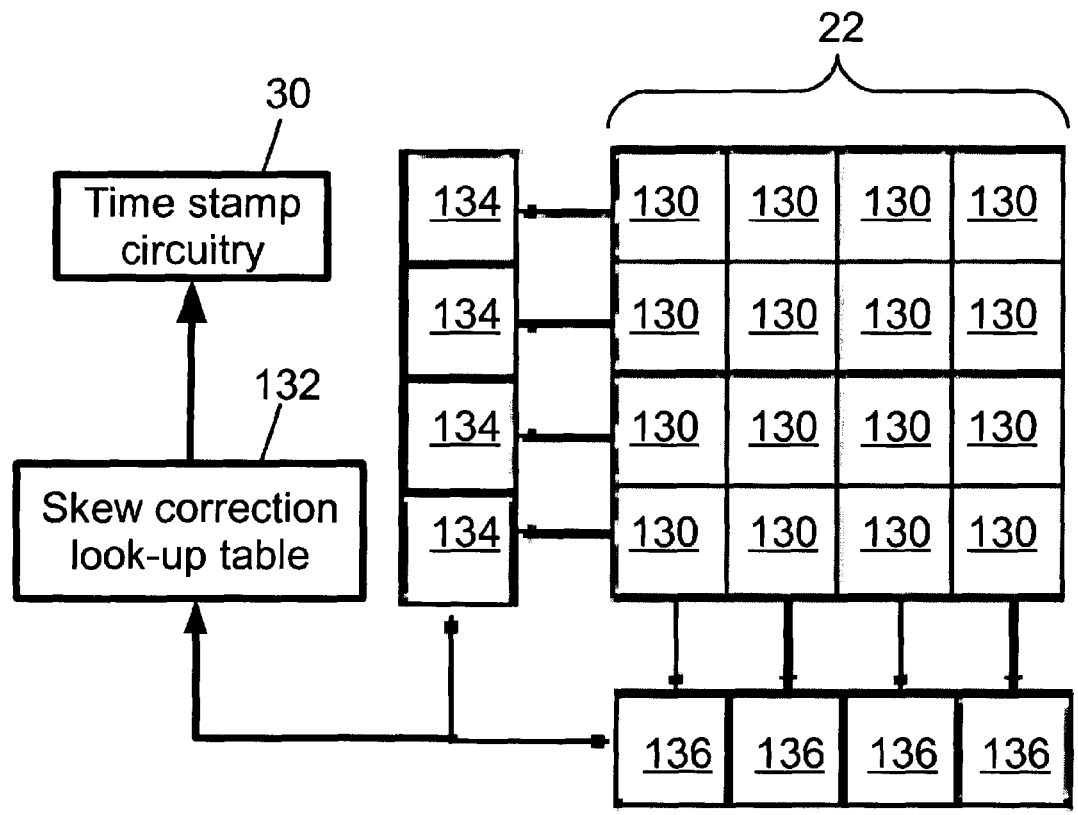
Figure 8:
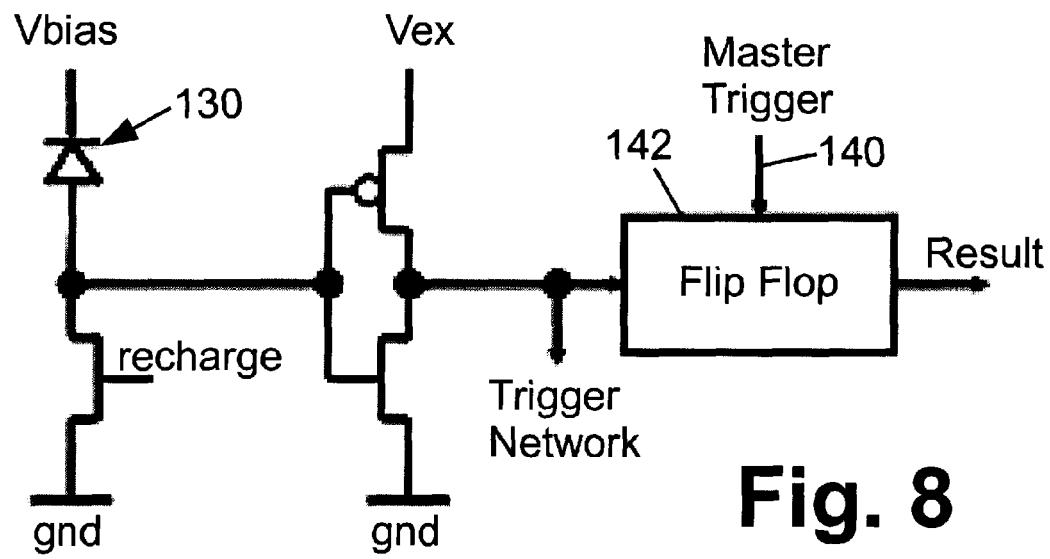

FIGS. 7 and 8 diagrammatically show first and second illustrative skew correction embodiments, respectively.

Figure 9:
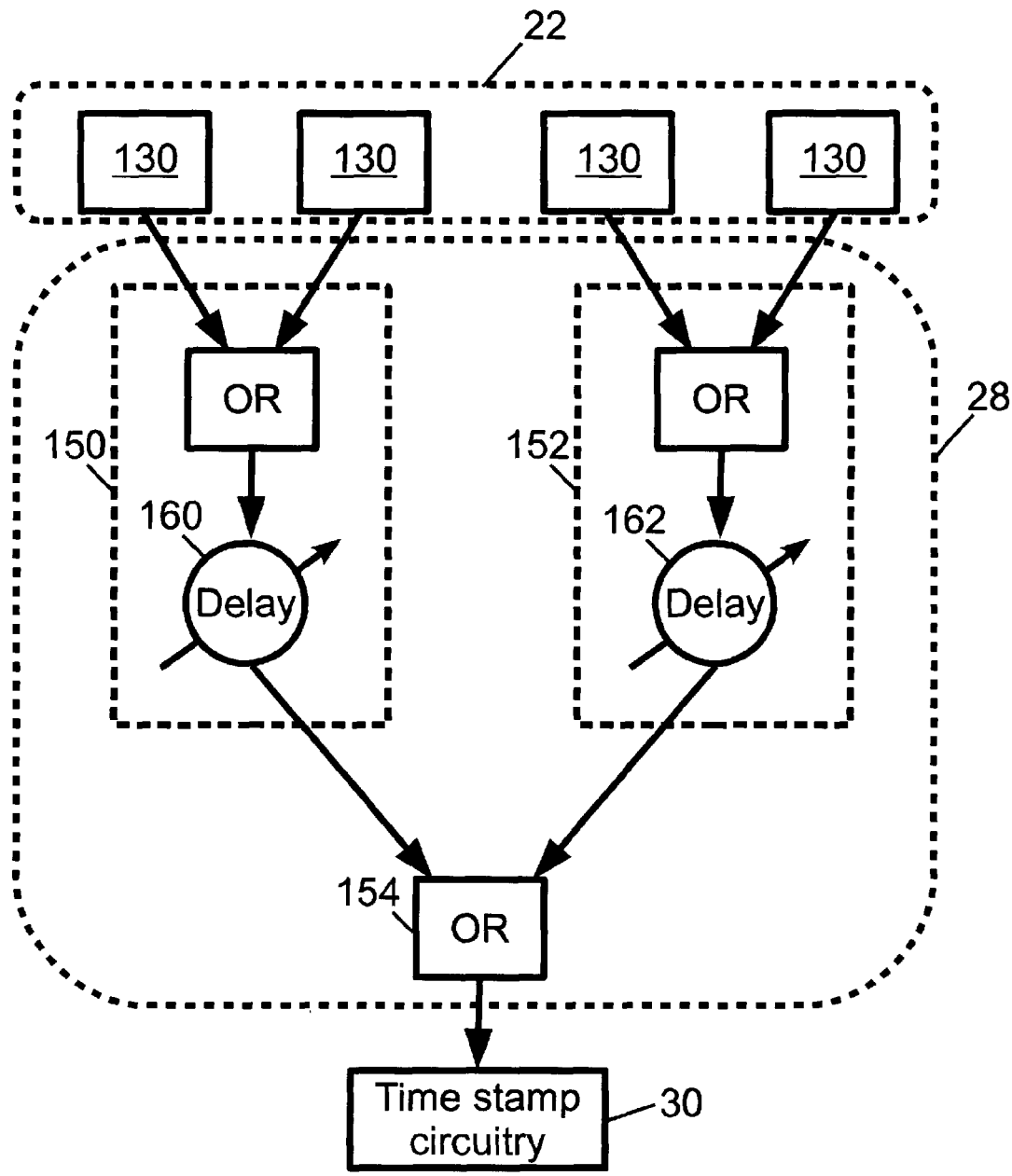

FIG. 9 diagrammatically shows an embodiment incorporating tunable delay elements into the trigger circuitry to provide skew correction.

With reference to FIG. 1, a time-of-flight positron emission tomography (TOF-PET) scanner 8 includes a plurality of radiation detectors 10 arranged to view an imaging region 12. In FIG. 1, the plurality of radiation detectors 10 are arranged in several rings of detectors along an axial direction; however, other arrangements of radiation detectors can be used. Moreover, it is to be appreciated that the plurality of radiation detectors 10 is diagrammatically illustrated; typically the radiation detectors are housed within a housing 14 of the scanner 8 and thus are not visible from the outside, and typically each ring of radiation detectors includes hundreds or thousands of radiation detectors. In some PET scanners, only a single ring of radiation detectors is provided, in others, two, three, four, five, or more rings of radiation detectors are provided. It should be appreciated that detector heads can be used in place of the detector ring structure shown in the Figures. The TOF-PET scanner 8 includes a couch 16 or other support for positioning a human patient or other imaging subject in the imaging region 12. Optionally, the couch 16 is linearly movable in the axial direction generally transverse to the rings of radiation detectors 10 to facilitate acquisition of three-dimensional imaging data. Additionally or alternatively, the imaging subject can be held stationary, and the plurality of rings of radiation detectors used to acquire three-dimensional TOF-PET imaging data. In yet other embodiments, only a single ring of detectors is provided, the imaging subject remains stationary, and the resulting image is two-dimensional.

A suitable radiopharmaceutical is administered to the patient or other imaging subject prior to initiation of TOF-PET imaging. The radiopharmaceutical includes a radioactive substance that undergoes radioactive decay events that emit positrons. The positrons rapidly annihilate with nearby electrons of the imaging subject. The resulting positron-electron annihilation event produces two oppositely directed gamma rays having energies of 511 keV. The gamma rays travel at the speed of light, i.e. $\sim 3 \times 10^8$ meters/sec. Since the imaging region 12 typically has a diameter or other characteristic dimension of about one meter or less (and more typically about 30-40 cm for a human imaging subject), the time-of-flight for a gamma particle from the position of the positron-electron annihilation event to one of the detectors of the plurality of radiation detectors 10 is about a few nanoseconds or less. Thus, the two oppositely directed gamma rays strike two of the radiation detectors substantially simultaneously.

With continuing reference to FIG. 1, a single detector pixel 20 of the annular ring of radiation detectors 10 is shown in diagrammatic representation including associated on-board electronics. The detector pixel 20 comprises an array of silicon-based single-photon avalanche diode (SPAD) detectors 22 viewing a scintillator 24 that produces a scintillation or burst of light when a (diagrammatically indicated) 511 keV gamma ray γ strikes the scintillator 24. The scintillator 24 is selected to provide high stopping power for 511 keV gamma rays with rapid temporal decay of the scintillation burst. Some suitable scintillator materials are LSO, LYSO, MLS, LGSO, LaBr and mixtures thereof, although other scintillator materials can also be used. The scintillation or burst of light is received by the array of detectors 22 which may, by way of illustrative example, be fabricated monolithically on a silicon substrate. An optional planar light pipe (not shown) can be interposed between the scintillator 24 and the array of detectors 22 to improve optical coupling between the scintillator 24 and the array of detectors 22. The scintillator 24 and optional light pipe are optionally encased in a reflective coating which directs scintillation light toward the array of detectors 22.

The use of the array of detectors 22, rather than a single detector, for the detector pixel 20 is due to the generation of a scintillation or burst of light responsive to the scintillator 24 absorbing the single 511 keV gamma ray γ. Each SPAD of the array of detectors 22 can in general detect a single photon—thereafter it must recover including rebuilding the electric field over the p/n junction of the avalanche diode. By using the array of detectors 22 a count accumulator 26 accumulates a count of single-photon detections, and this count correlates with the total energy of the absorbed particle (that is, the 511 keV gamma ray γ in the illustrative example). A higher energy particle would be expected to produce a higher count while a lower energy particle would be expected to produce a lower count. Thus, the total count of photon detections over the time interval of the scintillation event can be used in "energy windowing" to filter out detection events that are not likely (on the basis of total particle energy) to be 511 keV gamma rays associated with positron-electron annihilation events.

The array of detectors 22 has associated trigger circuitry 28 whose purpose is to generate a trigger signal associated with the detection event. In a typical approach, the trigger circuitry comprises a trigger network connected with all SPAD devices of the array of detectors 22, and the trigger network is configured to switch from a quiescent (or "off") state to a triggered (or "on") state responsive to a single SPAD detecting a photon. Alternatively, the switch can occur after a selected number of photon detections, and/or validation circuitry can be included, so as to reduce likelihood of generating a "false" trigger signal. The trigger signal is used by time stamp circuitry 30 to generate a digital time stamp for the detection event.

In an illustrative approach, the array of detectors 22 comprising SPAD devices may be fabricated monolithically on a silicon substrate. The trigger circuitry 28 may also be monolithically integrated on the same silicon substrate, in the same circuit layer as the SPAD devices (i.e., interleaved between SPAD rows/columns) or disposed in a separate circuit layer, e.g. below the array of SPAD devices. The associated count accumulation and time stamp electronics 26, 30 may also be monolithically integrated on the same silicon substrate as the array of detectors 22, or may be disposed on a separate silicon substrate connected with the detector array substrate. In either case, the electronics 26, 30 (or various portions thereof) may be variously embodied, for example as a field programmable gate array (FPGA), application-specific integrated circuitry (ASIC), suitably programmed microprocessor or microcontroller, various combinations of the foregoing, or so forth. While the single diagrammatically represented detector pixel 20 is described by way of illustrative example, it is to be understood that the PET detector ring 10 includes many thousands, tens of thousands, or more such detector pixels. Various numbers of detector pixels may be integrated on a single silicon substrate to form a detector module of (without loss of generality) N×M detector pixels (where each detector pixel includes an instance of the SPAD array 22). Some suitable detector pixels are set forth, by way of illustrative example, in: Frach et al., U.S. Pat. No. 7,723,694 issued May 25, 2010 which is incorporated herein by reference in its entirety; Fiedler et al, U.S. Pat. No. 7,626,389 issued Dec. 1, 2009 which is incorporated herein by reference in its entirety; and Prescher et al., U.S. Pub. No. 2010/0182011 A1 published Jul. 22, 2010 which is incorporated herein by reference in its entirety.

It is further to be appreciated that the disclosed detector pixel is merely an illustrative example, and other detector pixel configurations are also contemplated. For example, in a direct conversion detector pixel, a single detector is configured to directly absorb and detect the 511 keV gamma ray without the use of an intervening scintillator. In such an embodiment, the scintillator 24 is omitted, the array of detectors 22 is replaced by a single direct-conversion detector, and the trigger circuitry 28 is simplified to a single binary switch that activates when the single-particle detector is activated.

With continuing reference to FIG. 1, the circuitry 26, 30 generates, for each radiation particle detection event, a "list mode" set of data including the time stamp generated by the time stamp circuitry 30, the particle energy as represented by the photon count accumulated by the count accumulator 26, and spatial coordinates of the detector pixel 20. The list mode data for these events are suitably communicated off the PET scanner 8 to a suitable data processing device such as an illustrative computer 40, and are stored in a list mode data memory 42. The data processing device 40 implements suitable data processing. For PET data, the data processing device 40 suitably implements a 511 keV coincidence detector 44 that searches the list mode data to identify substantially simultaneous 511 keV particle detection events. The searching suitably employs an energy window to filter out particle detection events corresponding to particles having energies well above or well below 511 keV, and then employs a time window to identify remaining (at least approximately) 511 keV detection events that occurred as "substantially simultaneous" pairs, that is, two 511 keV detection events that occurred within a sufficiently small time window so that both detected 511 keV gamma rays could have originated from a single positron-electron annihilation event. Such a detected pair defines a "line of response" or LOR connecting the two detecting pixels. In the case of TOF PET, the small time difference between the two "substantially simultaneous" detection events is used to further localize the positron-electron annihilation event along the LOR.

The resulting energy- and coincidence-filtered 511 keV detection event pairs constitute a TOF PET data set that is suitably stored in a TOF PET data memory 46. This TOF PET data set is optionally reconstructed by a TOF PET data reconstructor 48 also suitably implemented by the computer or other data processing device 40 in order to reconstruct a PET image that is suitably stored in a TOF PET image memory 50, or displayed on a display device 52 integral with or in operative communication with the data processing device 40, or otherwise utilized. The TOF PET data reconstructor 48 may use substantially any suitable reconstruction algorithm, such as iterative forward/backward projection (including TOF localization of the projections), a filtered backprojection reconstruction algorithm, or so forth.

With continuing reference to FIG. 1 and with further reference to FIGS. 2 and 3, an illustrative embodiment of the time stamp circuitry and associated timing components is described. The time stamp processing is referenced to a coarse clock 60. To provide some quantitative examples herein, the clock 60 is assumed herein to produce a clock signal 62 cycling at 200 MHz (corresponding to a clock cycle period of 5 ns); however, it is to be understood that a faster or slower clock cycle can be employed. The illustrative clock signal 62 is a square wave having a 50% duty cycle; however, other waveforms can be employed for the clock signal. For illustrative simplicity, in FIG. 1 the clock 60 is shown as a component of the detector pixel 20; more typically, however, the clock is located elsewhere and the clock signal 62 is input to the detector pixel 20.

The clock signal 62 has a period of 5 ns, which is too coarse to provide the sub-nanosecond resolution desired for time stamping of 511 keV gamma ray detection events. To provide finer resolution, two time-to-digital converter (TDC) devices 70, 72 are provided. The first TDC 70 is also denoted herein as "TDC1" or as "fine counter 1" or "FC1", while the second TDC 72 is also denoted herein as "TDC2" or as "fine counter 2" or "FC2". While in principle a single TDC would be sufficient, as disclosed herein there are substantial advantages to employing the illustrated two TDC 70, 72. These advantages include elimination of "dead zones" in which one of the TDC 70, 72 provides unreliable results, and providing for automatic calibration of both TDC 70, 72 to compensate for drift in the output of the fine counter over time due to voltage and/or temperature variation.

With particular reference to FIG. 2, each TDC 70, 72 receives the same input from the trigger circuitry 28. Each TDC 70, 72 is synchronized with the common clock signal 62, which is used to synchronize respective fine counters 74, 76 that are used to measure the time difference between the detected event (as represented by the trigger signal generated by the trigger circuitry 28) and a reference feature of the first fine counter 74 (for TDC1 70) or the second fine counter 76 (for TDC2 72). The reference feature may be a rising edge, or a falling edge, or other suitable feature of the fine counters 74, 76. In the illustrative examples the latching will be to the rising edge $E_R$ of the fine counter 74, 76. The time difference measurement performed by each TDC 70, 72 is suitably based on a time-to-distance measurement according to one of tap line, a Vernier, a pulse-shrinking, and a constant current capacitor discharge, or the like. By way of illustrative example, some suitable TDC configurations are disclosed in Frach et al., U.S. Pub. No. 2009/0236532 A1 published Sep. 24, 2009 which is incorporated herein by reference in its entirety.

At the input of each TDC 70, 72, a respective storage element 80, 82, such as a flip-flop, latch, or the like, is latched when the trigger signal is present. If the input is stable the switch will latch at the subsequent rising edge $E_R$ of the respective fine counter 74, 76. However, if the trigger signal is received at the input during a meta-stable region, i.e. during the setup or hold times, the switch may become meta-stable and the trigger signal will not be latched until the next rising edge $E_R$ of the fine counter 74, 76 leading to a significant increase in the timestamp error.

If only a single TDC was provided, then there would be no way to accommodate this timestamp error. In the illustrative approach, however, two TDC 70, 72 are provided. To reduce timing errors stemming from meta-stability at the input, each TDC 70, 72 is synchronized to a different fine counter 74, 76 in a manner that ensures that at least one storage element 80, 82 will latch properly at any time.

With particular reference to FIG. 3, in the illustrative example the fine counter 76 of TDC2 72 is "out of phase" by 180° respective to the fine counter 74 of TDC1 70. This means that the rising edges $E_R$ of the fine counter 74 are "in between" the rising edges $E_R$ of the fine counter 76, and vice versa. Because of this, unstable or meta-stable regions 90 of TDC1 70 lie within the stable regions 92 of TDC2 72, and conversely unstable or meta-stable regions 94 of TDC2 72 lie within the stable regions 96 of TDC1 70. The two 180° out-of-phase fine counters 74, 76 are readily generated from the clock signal 62 as 100 MHz counters by frequency divide-by-2 circuits (not shown).

The approach of FIG. 3 is an illustrative example, and other approaches can be used to provide twin TDC with a fixed time offset. For example, a phase shift of other than 180° between the two fine counters can be used, or the two TDC can latch off different reference features. (As an example of the latter approach, the two TDC can use the same (in-phase) fine counter but have one TDC latch off the rising edge and the other TDC latch off the falling edge).

With returning reference to FIG. 2, the first TDC 70 computes a time difference 100 between the detected event (as represented by the trigger signal generated by the trigger circuitry 28) and a reference feature (e.g., rising edge) of the first fine counter 74. Similarly, the second TDC 72 computes a time difference 102 between the detected event and a reference feature of the second fine counter 76. These time differences 100, 102 typically do not directly equal the desired time stamp. Rather, a first transform operation is performed to convert the time difference 100 into a first time stamp TS1, and a second transform operation is performed to convert the time difference 102 into a second time stamp TS2. The transform operation determines the offset in time units and adds that offset to the reference time provided by the clock signal 62. In the illustrative embodiment, the first TDC 70 applies a first look-up table LUT1 in performing the transform that generates the first time stamp TS1, while the second TDC 72 applies a second look-up table LUT2 in performing the transform that generates the second time stamp TS2. The look-up tables LUT1, LUT2 optionally also identify respective select bits 104, 106 that indicate whether the detected event lies in one of the unstable or metastable regions 90, 94. Instead of look-up tables, a suitably calibrated empirical transform function may be employed. Further data processing circuitry 108 generates a final time stamp TS for the detection event based on the first and second timestamps TS1, TS2 generated by the twin TDC 70, 72. In one suitable approach, the circuitry 108 discards the output of a TDC if its select bits indicate the detected event lies in an unstable or metastable region for that TDC—necessarily, the detected event will lie in a stable region for the other TDC and so that TDC reading is used. If both TDC 70, 72 are stable, then the circuitry 108 may average or otherwise aggregate the first and second timestamps TS1, TS2 to generate the final timestamp TS.

With reference to FIGS. 4 and 5, a quantitative illustrative example of operation of the TDC 70, 72 and timestamp circuitry 30 is described. This example uses the clock signal 62 with frequency 200 MHz, and uses the two fine counters 74, 76 with frequency 100 MHz and 180° phase offset, as shown in FIG. 3. The fine counters 74, 76 thus have periods of 10 ns (that is, twice the 5 ns period of the clock signal 62). The bin width of each TDC varies. The look-up tables LUT1, LUT2 are therefore used to translate the fine counter values in relative time units to the absolute time reference of the 200 Mhz system clock signal 62. FIG. 4 diagrammatically illustrates possible look-up table values for TDC1, TDC2 70, 72 respectively. In this example the accuracy of the TDC is 9 bits over a period of 10 ns, so that each "bin" has a width 10 ns/512~19.5 ps. The look-up tables LUT1, LUT2 can be generated in various ways, such as using a delay line measurements, or random hits measurements, or so forth.

FIG. 5 illustrates use of the TDC 70, 72 with look-up tables LUT1, LUT2 for time stamp measurements. The CC1 and CC2 indicates clock cycles of the fine counters 74, 76 of the TDC 70, 72 each operating at 100 Mhz. Each increment of the clock cycle CC indicates an increment of 512 which is 10 ns. The first time stamp TS1 generated by the first TDC 70 is given by CC1+LUT(FC1), where LUT(FC1) indicates the output of the look-up table LUT1 for the fine counter input designated "FC1". Analogously, the second time stamp TS2 generated by the second TDC 72 is given by CC2+LUT (FC2)+256, where the offset 256 corresponds to 5 ns. Whether the circuitry 108 selects the first time stamp TS1 output by TDC1 70 or the second time stamp TS2 output by TDC2 72, or an average of these two, depends upon the location in the time axis. For example, at times when TDC 1 70 has no valid timestamp generation (regions 90 indicated in FIG. 3, around 0 ns in the example of FIG. 5), the second time stamp TS2 output by TDC2 72 is selected as the output time stamp TS. Averaging of the two time stamps TS1, TS2 when both TDC 70, 72 are stable is advantageous to reduce jitter.

With returning reference to FIG. 1, another advantage recognized herein of using two TDC 70, 72 is that this enables providing an automatic TDC calibration circuit 120 for calibrating both TDC 70, 72 to compensate for drift in the output of the fine counters 74, 76 over time due to voltage and/or temperature variation. TDC autocalibration approaches disclosed herein take advantage of two observations. First, the drift of the two TDC 70, 72 can be expected to be identical or nearly so. This is a consequence of the two TDC 70, 72 being in the same environment (and hence at the same temperature, experiencing the same ambient humidity, and so forth) and being driven by a common voltage source (so that any voltage variation should be the same for both TDC 70, 72).

The second observation made herein is that the second TDC 72 should always have the same fixed time offset respective to the first TDC 70. (Or, turned around, the first TDC 70 should always have the same fixed time offset respective to the second TDC 72). This is a consequence of the two TDC 70, 72 being synchronized with the common clock signal 62. As best seen in FIG. 3, in the illustrative embodiment the fixed time offset between the two TDC 70, 72 should be precisely 5 ns corresponding to one period of the clock signal 62; however, depending upon the phase offset of the two fine counters, or the (optionally different) choice of reference features for use in the two TDC, the fixed time offset may be different.

The second TDC 72 should always have the same fixed time offset respective to the first TDC 70. It therefore follows that if the time difference between the second time stamp TS2 and the first time stamp TS1 is different from this fixed time offset, then this difference is due to drift over time of the two TDC. Moreover, the direction of the drift is readily ascertained. If the time difference between the second time stamp TS2 and the first time stamp TS1 is less than the fixed time offset, then the fine counters 74, 76 have periods that are too short—this can be corrected by a multiplication factor incorporated into the transform that is greater than one. On the other hand, if the time difference between the second time stamp TS2 and the first time stamp TS1 is greater than the fixed time offset, then the fine counters 74, 76 have periods that are too long—this can be corrected by a multiplication factor incorporated into the transform that is less than one.

In view of the foregoing, the TDC autocalibration circuit 120 employs the following algorithm: upon detecting an event, a trigger signal associated with the detection of the event is generated, the first time stamp TS1 for the trigger signal is generated using the first TDC 70, and the second time stamp TS2 for the trigger signal is generated using the second TDC 72. A time calibration of the two TDC 70, 72 is then calculated responsive to the time difference between the second time stamp TS2 and the first time stamp TS1 being different from the a priori-known fixed time offset.

In a suitable approach, the first time stamp TS1 is generated by the first TDC 70 by measuring the first time interval 100 (using the fine counter 74) and transforming the first time interval 100 into the first time stamp TS1 using a first transform operation (including applying the look-up table LUT1 in the illustrative embodiment). Similarly, the second time stamp TS2 is generated by the second TDC 72 by measuring the second time interval 102 (using the fine counter 76) and transforming the second time interval 102 into the second time stamp TS2 using a second transform operation (including applying the look-up table LUT2 in the illustrative embodiment). The adjusting then comprises adjusting the first and second transform operations responsive to the time difference between the second time stamp TS2 and the first time stamp TS1 being different from the fixed time offset. In one suitable approach, this is done by including into the first transform operation a multiplication factor, and including into the second transform operation the (same) multiplication factor. The adjusting then comprises increasing the multiplication factor if the time difference between the second time stamp TS2 and the first time stamp TS1 is smaller than the fixed time offset, and decreasing the multiplication factor if the time difference between the second time stamp TS2 and the first time stamp TS1 is larger than the fixed time offset.

With reference to FIG. 6, an illustrative embodiment of the TDC autocalibration circuit 120 is described. The circuit of FIG. 6 is configured for the quantitative example disclosed herein in which the clock signal 62 has a frequency of 200 MHz, each fine counter 74, 76 has a frequency of 100 MHz and the two fine counters 74, 76 are offset in phase by 180°, and the accuracy of each TDC 70, 72 is 9 bits over a period of 10 ns, so that each "bin" has a width 10 ns/512~19.5 ps. The difference between the time stamp TS1 output by the look-up table LUT1 of TDC1 70 and the time stamp TS2 output by the look-up table LUT2 of TDC2 72 should be always 256 (which correspondents with 5 ns). This is the fixed time offset in this quantitative example. However, the actual time difference between the second time stamp TS2 and the first time stamp TS1 will change if the slopes of the fine counters 74, 76 drift, for example due to voltage and/or temperature variation. A multiplicative correction factor M for correcting the slopes can be generated based on the time difference between the first and second time stamps TS1, TS2 and the a priori-known fixed time offset (e.g., 256 or 5 ns).

The TDC calibration circuit 120 of FIG. 6 is activated each time an event is processed to be assigned a time stamp. The TDC 70, 72 generate respective outputs 100, 102 which are multiplied by the multiplication factor M (also denoted "mul_factor" herein) which will initially be set to 1.0 (corresponding to no correction). The results 100, 102 are input to the respective look-up tables LUT1, LUT2. The resulting time stamps TS1, TS2 are compared at a comparator 122, and a decision block 124 generates a feedback signal 126 that is used to adjust the multiplication factor M (if an adjustment is needed). If the distance determined by the comparator 122 is above 256 (meaning the slope is too steep) then the feedback signal 126 is suitably a "do_deer" signal that causes the multiplication factor M to be decremented by a selected amount (for example, if the multiplication factor M or "mul_factor" has an accuracy of 12 bits and is represented in a hexadecimal notation, then the decrement may be from 0x800 to 0x7FF).

Conversely, if the slope is too shallow, then the feedback signal 126 is a "do_incr" signal that causes the multiplication factor M to be incremented by the selected amount so as to compensate for the too shallow slope. Still further, if the slope is correct such that the TS1, TS2 difference equals 256 then the feedback signal 126 is "hold" which causes no change in the multiplication factor M.

When the next event is detected and its trigger signal propagated to the time stamp circuitry 30 for time stamping, the TDC calibration circuit 120 is again invoked, this time with the multiplication factor M slightly less than 1.0. The outputs 100, 102 are now multiplied with a mul_factor which is somewhat below 1.0 so as to provide correction for the "too steep" slopes. This will be continued for every event detection/timestamping so that the multiplication factor M (mul_factor) is adjusted to compensate for any drift to maintain the fixed time offset of (in this quantitative example) 256 (or 5 ns).

If one of the TDC 70, 72 is in an unstable or meta-stable condition (e.g., state 90 for TDC 70 or state 94 for TDC 72 as indicated in FIG. 3, which condition is indicated by suitable values of the select bits 104, 106 shown in FIG. 2) the corresponding iteration of operation of the TDC calibration circuit 120 is optionally skipped.

The approach of the TDC autocalibration circuit 120 of FIG. 6 employs the increment "do_incr" or decrement "do_decr" of fixed magnitude, and the feedback signal 126 identifies only the "direction" of adjustment of the multiplication factor M. This approach is suitable assuming that the TDC drift is relatively slow, as is expected for drift caused by temperature and/or voltage variation, so that iterative incrementing or decrementing of the multiplication factor M can keep up with the slow drift. In another contemplated approach, both the direction and the magnitude of the feedback signal 126 is computed based on the magnitude of the timestamp TS1, TS2 difference so as to provide a single adjustment of the multiplication factor M that should correct the drift in a single adjustment (that is, not incrementally). This approach entails modifying the decision block 124 to compute the magnitude of the feedback signal 126 based on the magnitude of the difference between the timestamps TS1, TS2.

The TDC autocalibration circuit 120 described with particular reference to FIGS. 1 and 6 provides compensation for temporal drift of the TDCs. In embodiments in which the detector pixel comprises a two-dimensional array of detectors (e.g., a two-dimensional array of SPAD), the pixel also optionally includes correction for skew. The source of skew error is that the trigger signal corresponding to an event detection (e.g., a 511 keV particle detection in the case of PET imaging) is generated by a single triggering detector of the array of detectors. If the temporal characteristics of this triggering varies amongst the detectors of the array of detectors, then the trigger signal timing depends upon which detector acted as the triggering detector. Such variation can be reduced by configuring the trigger circuitry 28 in a "balanced" fashion such that the propagation path length from any detector of the array of detectors to the time stamp circuitry 30 is always the same. See, for example, Prescher et al., WO 2009/019660 A2 published Feb. 12, 2009 and incorporated herein by reference in its entirety for some illustrative trigger circuits designed to reduce skew. Nonetheless, even with balancing of the trigger circuitry 28 during detector array design, it is expected that process variations may result in substantial skew being observed in the detector array.

The approaches for skew correction disclosed herein are based upon assessing the skew by measuring propagation time of a trigger signal from each detector to the time stamp circuitry 30, and correcting the skew based on these measurements. The measurement step can employ various manual, automated, or semi-automated measurement procedures. In an optical approach, a laser generating picosecond light pulses is applied to individual SPAD cells of the detector array, and a map of the delay between the laser pulse and the time stamp across the detector array provides data for assessing skew of the detector array. Instead of optically activating individual SPAD cells, dedicated current injection circuitry may be provided in the detector array. In some embodiments the detector array includes inhibit logic that can "turn off" the triggering capability of selected SPAD cells, so that the triggering characteristics of individual SPAD cells can be characterized in isolation. See, e.g., Frach et al., U.S. Pat. No. 7,723,694 issued May 25, 2010 which is incorporated herein by reference in its entirety.

With reference to FIG. 7, once the skew characteristics of each SPAD 130 of the array of detectors 22 is characterized, this information is used to create a skew correction look-up table 132. The position of the triggering SPAD cell that detected the first photon is stored. In the embodiment of FIG. 7, this is accomplished by a set of row flip-flops 134 and a set of column flip-flops 136 that together store the (row,column) index if the triggering SPAD cell at the periphery of the pixel detector array 22. The (row,column) coordinates are input to the skew correction look-up table 132 which outputs the skew correction for the triggering SPAD cell to the time stamp circuitry 30 (see FIG. 1) for use in correcting the time stamp. In a typical approach, the skew correction look-up table 132 stores time offsets, and the time offset for the triggering SPAD cell is added to (or, in some embodiments and for some triggering SPAD cells, possibly subtracted from) the time stamp TS to generate the skew-corrected time stamp.

With reference to FIG. 8, in an alternative embodiment the position of the triggering SPAD cell is stored at the individual SPAD cell. The master trigger signal 140 (used to start the TDC) is fed back to each SPAD cell, with minimum delay to minimize the number of multiple detections, and this signal 140 is then used to latch the status of the cell via a flip-flop 142. This information is input to the skew correction look-up table 132 as in FIG. 7 (aspect not shown in FIG. 8) for generating the skew correction.

With reference to FIG. 9, in another approach the trigger circuitry 28 is modified by the addition of tunable delay elements in order to correct the skew. As shown in FIG. 9, the trigger circuitry 28 suitably comprises a network of signal combining nodes, of which FIG. 9 shows signal combining nodes 150, 152, 154 by way of illustrative example. The trigger signal originates at a triggering SPAD cell of the set of SPAD cells comprising the detector array 22, and the trigger signal propagates through the nodes 150, 152, 154 of the trigger circuitry 28 to reach the time stamp circuitry 30. The network of nodes is optionally balanced so that the trigger signal traverses the same number of nodes to reach the time stamp circuitry 30 regardless of which SPAD cell 130 serves as the triggering SPAD cell. Nonetheless, some differences in the total trigger signal propagation may occur depending upon which SPAD cell is the triggering SPAD cell.

Toward this end, selected nodes, such as the illustrative nodes 150, 152, include respective delay elements 160, 162 that are tunable to correct any skew. The delay elements 160, 162 may, for example, comprise digitally controlled delay elements such as are described in Maymandi-Nejad et al., "A Digitally Programmable Delay Element: Design and Analysis", IEEE Trans. on Very Large Scale Integration (VLSI) Systems vol. 11 no. 5 pages 871-878 (2003) which is incorporated herein by reference in its entirety. Other types of delay elements may be used, such as a designed buffer circuit or buffers with variable loads.

The delay elements 160, 162 are tunable in that the delay introduced by each delay element 160, 162 is individually configurable. Based on the skew measurements the delays imposed by the delay elements 160, 162 are set to correct for skew. A delay element can be placed at each node or, alternatively, at a subset of nodes (as in FIG. 9, where nodes 150, 152 include respective delay elements 160, 162 but the node 154 does not include a delay element). The range and the minimum adjustable delay step of each delay element 160, 162 can be chosen based on its position in the trigger network.

The approach of FIG. 9 in which delay elements 160, 162 are included in the trigger circuitry 28 has certain advantages. The skew is corrected independent of the number of detected photons. Additionally, the design condition of balance of the trigger network can be relaxed since any imbalance in the trigger network can be compensated by adjustment of the delay elements 160, 162.

The disclosed detectors with time stamping having increased robustness against temporal drift and spatial skew are described with illustrative reference to TOF PET, as illustrated diagrammatically in FIG. 1. However, the disclosed detectors will find more general application, for example in single photon detector arrays used in various instruments and areas of astronomy, physics, and so forth.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A method comprising:
   (i) synchronizing a first time-to-digital converter (TDC) with a common clock signal;
   (ii) synchronizing a second TDC with the common clock signal wherein the synchronizing operations (i) and (ii) determine a fixed time offset of the second TDC respective to the first TDC as the period of the common clock signal or as a fixed fraction or multiple of the period of the common clock signal;
   detecting an event;
   generating a trigger signal associated with the detection of the event;
   generating a first time stamp for the trigger signal by measuring a first time interval using the first TDC and transforming the first time interval into the first time stamp using a first transform operation including multiplying by a multiplication factor;
   generating a second time stamp for the trigger signal by measuring a second time interval using the second TDC and transforming the second time interval into the second time stamp using a second transform operation including multiplying by the multiplication factor;
   associating a time stamp with the event based on the first time stamp and the second time stamp; and
   increasing or decreasing the multiplication factor to reduce any difference between (1) the time difference between the second time stamp and the first time stamp and (2) the fixed time offset.

2. The method of claim 1, wherein the increasing or decreasing comprises:
   increasing the multiplication factor if the time difference between the second time stamp and the first time stamp is smaller than the fixed time offset; and
   decreasing the multiplication factor if the time difference between the second time stamp and the first time stamp is larger than the fixed time offset.

3. The method of claim 1, wherein the first transform operation includes applying a first look-up table and the second transform operation includes applying a second look-up table.

4. The method of claim 1, wherein the detecting is performed using an array of detectors, the trigger signal is generated by a triggering detector of the array of detectors, and the method further comprises:
   delaying the trigger signal by a delay time selected based on the triggering detector.

5. The method of claim 4, wherein the delaying comprises:
   providing tunable delay elements in a trigger signal network associated with the array of detectors; and
   setting delay times for the tunable delay elements to compensate skew of the array of array of detectors.

6. The method of claim 1, wherein the detecting is performed using an array of detectors, the trigger signal is generated by a triggering detector of the array of detectors, and the method further comprises:
   adjusting the first time stamp and the second time stamp based on the triggering detector.

7. The method of claim 1, wherein the associating comprises:
   associating the event with one of (i) the first time stamp, (ii) the second time stamp, and (iii) an aggregation of the first time stamp and the second time stamp;
   wherein the associating selects between (i), (ii), and (iii) based on an assessment of reliability of the first time stamp and of the second time stamp.

8. The method of claim 1, wherein the detecting comprises detecting a radiation particle using an array of positron emission tomography (PET) detectors, and the method further comprises:
   repeating the detecting, generating of the trigger signal, generating of first and second time stamps, and associating to acquire a data set of time stamped radiation detection events;
   generating a time-of-flight (TOF) PET data set from the data set of time stamped radiation detection events; and
   reconstructing the TOF PET data set to generate a PET image.

9. An apparatus comprising:
   a detector configured to detect an event;
   a first time-to-digital converter (TDC) configured to generate a first time stamp for the detection of the event by measuring a first time interval and transforming the first time interval into the first time stamp using a first transform operation including multiplying by a multiplication factor;
   a second TDC configured to generate a second time stamp for the detection of the event by measuring a second time interval and transforming the second time interval into the second time stamp using a second transform operation including multiplying by the multiplication factor, there being a fixed time offset between the second TDC and the first TDC; and
   an autocalibration circuit configured to adjust the multiplication factor to keep the time difference between the second time stamp and the first time stamp equal to the fixed time offset between the second TDC and the first TDC.

10. The apparatus of claim 9, wherein:
the first TDC and the second TDC are both synchronized with a common clock signal that defines the fixed time offset between the second TDC and the first TDC as the period of the common clock signal or as a fixed fraction or multiple of the period of the common clock signal.

11. The apparatus of claim 9, wherein the autocalibration unit is configured to increase the multiplication factor if the time difference between the second time stamp and the first time stamp is smaller than the fixed time offset and to decrease the multiplication factor if the time difference between the second time stamp and the first time stamp is larger than the fixed time offset.

12. The apparatus of claim 9, wherein the first transform operation further includes applying a first look-up table and the second transform operation further includes applying a second look-up table.

13. The apparatus of claim 9, wherein the detector comprises an array of detectors and the apparatus further comprises:
trigger circuitry configured to propagate a trigger signal associated with the detection of the event from a triggering detector of the array of detectors to the first and second TDC's, the trigger circuitry including delay elements configured to delay propagation of the trigger signal based on which detector is the triggering detector.

14. The apparatus of claim 9, wherein the detector comprises an array of detectors and the apparatus further comprises:
trigger circuitry configured to propagate a trigger signal associated with the detection of the event from a triggering detector of the array of detectors to the first and second TDC's; and
skew correction circuitry configured to adjust a timestamp generated from the first timestamp and the second timestamp based on which detector is the triggering detector.

15. The apparatus of claim 9, wherein the detector comprises an array of silicon-based single photon avalanche detector (SPAD) cells.

16. A positron emission tomography (PET) system including:
radiation detectors comprising the apparatus of claim 9; and
a processing device configured to generate time-of-flight (TOF) PET data from the output of the radiation detectors and to reconstruct the TOF PET data to generate an image.

17. An apparatus comprising:
an array of detectors configured to detect an event;
trigger circuitry configured to propagate a trigger signal associated with the detection of the event from a triggering detector of the array of detectors to time stamp circuitry configured to generate a digital time stamp for the detection of the event using a time-to-digital converter (TDC);
a set of row flip-flops and a set of column flip-flops at the periphery of the array of detectors that store the (row, column) index of the triggering detector of the array of detectors;
skew correction circuitry configured to adjust the generated digital time stamp by adding or subtracting a skew correction time offset for the triggering detector obtained from a skew correction look-up table tabulating the skew correction time offset for each detector of the array of detectors by (row, column) index;
a first time-to-digital converter (TDC) configured to generate a first time stamp for the detection of the event based on the trigger signal;
a second TDC configured to generate a second time stamp for the detection of the event based on the trigger signal; and
an autocalibration circuit configured to adjust a single multiplication factor applied to both the first TDC and the second TDC to keep the time difference between the second time stamp and the first time stamp equal to a predetermined fixed time offset between the second TDC and the first TDC.

18. The apparatus of claim 10, wherein the autocalibration circuit is configured to adjust the multiplication factor by feedback control to keep the time difference between the second time stamp and the first time stamp equal to the fixed time offset between the second TDC and the first TDC.

* * * * *